(12) United States Patent
Feng et al.

(10) Patent No.: US 12,735,669 B2
(45) Date of Patent: Sep. 15, 2026

(54) DEVICE AND METHOD FOR SEPARATING SINGLE COLONY IN DEEP-SEA IN-SITU ENVIRONMENT

(71) Applicants: GUANGDONG UNIVERSITY OF TECHNOLOGY, Guangdong (CN); GUANGDONG LABORATORY OF SOUTHERN OCEAN SCIENCE AND ENGINEERING (GUANGZHOU), Guangdong (CN)

(72) Inventors: Jingchun Feng, Guangdong (CN); Song Zhong, Guangdong (CN); Si Zhang, Guangdong (CN); Zhifeng Yang, Guangdong (CN); Yi Wang, Guangdong (CN); Yanpeng Cai, Guangdong (CN)

(73) Assignees: GUANGDONG UNIVERSITY OF TECHNOLOGY, Guangdong (CN); GUANGDONG LABORATORY OF SOUTHERN OCEAN SCIENCE AND ENGINEERING (GUANGZHOU), Guangdong (CN)

( * ) Notice: Subject to any disclaimer, the term of this patent is extended or adjusted under 35 U.S.C. 154(b) by 749 days.

(21) Appl. No.: 18/021,178

(22) PCT Filed: Mar. 30, 2022

(86) PCT No.: PCT/CN2022/084115

§ 371 (c)(1),
(2) Date: Feb. 14, 2023

(87) PCT Pub. No.: WO2023/173493

PCT Pub. Date: Sep. 21, 2023

(65) Prior Publication Data

US 2024/0263126 A1 Aug. 8, 2024

(51) Int. Cl.
*C12M 1/00* (2006.01)
*C12M 1/26* (2006.01)
(Continued)

(52) U.S. Cl.
CPC ............ *C12M 41/14* (2013.01); *C12M 29/00* (2013.01); *C12M 33/00* (2013.01); *C12M 41/40* (2013.01); *C12N 1/02* (2013.01); *C12N 1/20* (2013.01)

(58) Field of Classification Search
None
See application file for complete search history.

(56) References Cited

U.S. PATENT DOCUMENTS

2018/0112173 A1 4/2018 Wiles et al.
2022/0041973 A1* 2/2022 Stine ...................... C12M 41/48

FOREIGN PATENT DOCUMENTS

CN 103540521 1/2014
CN 103540521 A * 1/2014 ............ C12M 29/14
(Continued)

OTHER PUBLICATIONS

Translation of CN 209702757 U, Xiang, Shi-yu, Nov. 29, 2019 (Year: 2019).*

(Continued)

*Primary Examiner* — Henry H Nguyen
(74) *Attorney, Agent, or Firm* — JCIPRNET

(57) ABSTRACT

The present invention provides a device for separating a single colony in a deep-sea in-situ environment. The device includes a separation operation incubator, a liquid injection unit, a sampling unit, and a sampling probe device. The present invention further provides a method for separating a single colony in a deep-sea in-situ environment. The method includes: under the condition of maintaining the pressure and temperature in the separation operation incubator con- (Continued)

sistent with those of a culture environment of deep-sea microorganisms, injecting a microbial bacterial liquid into the separation operation incubator through the liquid injection unit; carrying out dipping and streaking operations by the sampling probe device; then, carrying out separation and culture; and at last, selecting a single colony by the sampling unit to realize separation of a single colony.

16 Claims, 3 Drawing Sheets

(51) Int. Cl.

| | |
|---|---|
| ***C12M 1/34*** | (2006.01) |
| ***C12N 1/02*** | (2006.01) |
| ***C12N 1/20*** | (2026.01) |

(56) References Cited

FOREIGN PATENT DOCUMENTS

| | | | |
|---|---|---|---|
| CN | 104195041 | 12/2014 | |
| CN | 106935120 A * | 7/2017 | ............ G09B 23/24 |
| CN | 109517723 | 3/2019 | |
| CN | 209702757 | 11/2019 | |
| CN | 111551671 A * | 8/2020 | .......... G01M 3/2815 |
| CN | 112048439 | 12/2020 | |
| CN | 112300908 | 2/2021 | |
| CN | 212655789 | 3/2021 | |
| JP | H0440884 | 2/1992 | |

OTHER PUBLICATIONS

Translation of CN 111551671 A, Feng, Jing-chun, Aug. 18, 2020 (Year: 2020).*

Translation of CN 103540521 A, Zhang, Yu, Jan. 29, 2014 (Year: 2014).*

Jiang Kail et al., “Equipment simulating seafloor extreme environment with remote monitor function”, Chinese Journal of Scientific Instrument, with English abstract, Sep. 2006, pp. 1-5.

Li Shi-Lun et al., “Control system of simulating platform for deep-sea extreme environment”, Journal of Zhejiang University(Engineering Science), with English abstract, Nov. 2005, pp. 1-4.

Jianzhen Liang et al., “Role of deep-sea equipment in promoting the forefront of studies on life in extreme environments”, iScience, Nov. 19, 2021, pp. 1-21.

“International Search Report (Form PCT/ISA/210) of PCT/CN2022/084115,” mailed on Nov. 25, 2022, pp. 1-5.

* cited by examiner

DEVICE AND METHOD FOR SEPARATING SINGLE COLONY IN DEEP-SEA IN-SITU ENVIRONMENT

CROSS-REFERENCE TO RELATED APPLICATION

This application is a 371 of international application of PCT application serial no. PCT/CN2022/084115, filed on Mar. 30, 2022, which claims the priority benefit of China application no. 202210264116.0, filed on Mar. 17, 2022. The entirety of each of the above mentioned patent applications is hereby incorporated by reference herein and made a part of this specification.

TECHNICAL FIELD

The present invention relates to the technical field of marine microorganisms, and in particular to a device and method for separating a single colony in a deep-sea in-situ environment.

BACKGROUND

Different from the land, the marine environment is a unique ecological environment, and has high salinity, high permeability, high pressure, oligotrophy, and other characteristics. Some sea areas also have high acidity, high alkalinity, hypoxia, low temperature, high temperature, high radiation, and other special conditions. Compared with some ecological environments on the land, the marine environment has no intense activities of microorganisms, but has abundant microbial resources from the sea surface to seabed sediments. Due to high innovativeness and diversity in genes, physiological metabolism, and the like, marine microorganisms play an irreplaceable role in promoting energy transfer and material circulation in the sea, maintaining the stability of the sea and even the global ecosystem, and the like.

At present, the marine microorganisms are separated mainly by separating a single colony under normal pressure after the pressure is released. As a result, special bacteria, such as barophilic bacteria, which originally exist in the marine environment have not been separated, and relatively few marine microorganisms have been separated. In addition, special target bacteria with high abundance have already been obtained by enrichment culture for a long term, so that streaking of a single colony under pressure-holding conditions is achieved. However, how to select and successfully culture a single colony has not yet been solved, so that the understanding of the marine microorganisms and the development and utilization of resources are further limited.

In view of this situation, a deep-sea microbial culture cabin is disclosed in the prior art. The deep-sea microbial culture cabin includes a linear bearing, a tension spring, a pressure compensation chamber, a fixed top plate, a deep-sea motor assembly, a fixed bottom plate, a hose, and a culture cabin body. According to this solution, the deep-sea motor assembly is rotated to open an end cover of the culture cabin body, so that enrichment culture of microorganisms in a completely open state is achieved. During placement and recovery, the end cover of the culture cabin body is closed, so that the microorganism culture cabin is sealed. Although the enrichment culture of the microorganisms in a deep-sea in-situ state can be achieved by using the culture cabin, separation and culture of the marine microorganisms are also carried out, and the successful culture rate cannot be effectively increased.

SUMMARY

In order to overcome at least one of the above-mentioned technical defects, the present invention provides a device and method for separating a single colony in a deep-sea in-situ environment. The separation and culture of a single colony in a high pressure environment are achieved, and the problem that deep-sea microorganisms are difficult to separate and culture is solved.

In order to solve the above-mentioned technical problems, the present invention adopts the following technical solutions.

A device for separating a single colony in a deep-sea in-situ environment includes a central control system, a separation operation incubator, an environmental parameter detection unit, a pressure control unit, a temperature control unit, a liquid injection unit, and a sampling unit. The separation operation incubator includes a base, and a cover fixedly connected to the base. The cover is used as an observation area and a separation operation area, and the base is used as a culture area. The observation area is used for observation of separation and culture processes. An inner slide rail is arranged in the separation operation area according to separation operation needs. A sampling probe device capable of sliding on the inner slide rail is installed on the inner slide rail, and used for carrying out a streaking operation and a sampling operation on microorganisms. A culture medium is arranged in the culture area, and used for culturing streaked microbial colonies. The environmental parameter detection unit is arranged in the separation operation incubator, and used for detecting temperature and pressure changes in the separation operation incubator in real time and transmitting data to the central control system. The pressure control unit and the temperature control unit are respectively connected to the separation operation incubator to ensure that the pressure and temperature in the separation operation incubator are consistent with a growth and culture environment of microorganisms. The liquid injection unit is used for injecting an enriched microbial bacteria liquid into the separation operation incubator to achieve dipping and streaking by the sampling probe device. The sampling unit is used for carrying out pressure-holding sampling on microorganisms. A control end of the sampling probe device, a control end of the pressure control unit, a control end of the temperature control unit, a control end of the liquid injection unit, and a control end of the sampling unit are all electrically connected to the central control system. A data output end of the observation area is electrically connected to the central control system.

In the above-mentioned solution, the base and cover are sealed and connected by a buckle. The base similar to a cylinder, the cover has a shape similar to that of an "L". The inner slide rail is a three-dimensional slide rail. The sampling probe device can slide up, down, left, and right on the inner slide rail, mainly to ensure that the sampling probe device can contact the surface of the culture medium in the base, and also be located above the culture medium in the base, so that convenience is provided for the sampling probe device to carry out various operations on the culture medium. The sampling probe device is mainly controlled by using the central control system to control a pressure-holding chip of the sampling probe device and to control the sampling probe device to be displayed.

In the above-mentioned solution, the central control system includes a server, a computer, and the like, and is used for realizing recording of changes in various environmental data information of enriched marine microorganisms during separation and culture in a high pressure environment and for realizing real-time acquisition, processing, storage the data information, and image output.

In the above-mentioned solution, a single colony is separated, selected, and cultured under pressure-holding conditions by establishing a single colony separation device. At last, a target bacterium can be obtained. The cultivability of marine microorganisms is effectively improved, and a basic solution is provided for separation and culture of the marine microorganisms. According to the above-mentioned solution, the enriched marine microorganisms can be separated under pressure-holding conditions in an in-situ high pressure environment, so that requirements of subsequent culture, functional identification, and the like are met.

The observation area includes an outer slide rail arranged on an outer side surface of the cover, a connection bracket slidably connected to the outer slide rail, an observation device fixed to an end of the connection bracket, and a visible window arranged on a surface of the cover. A data output end of the observation device is electrically connected to the central control system.

In the above-mentioned solution, the visible window is a circular visible window arranged in the center of the cover, so that convenience is provided for the observation device to observe the inside of the separation operation incubator. The outer slide rail is a horizontal slide rail, the telescopic L-shaped connection bracket is installed on the slide rail, and the observation device is arranged at the end of the connection bracket to facilitate observation and identification of microorganisms. For example, when an optical observation module of a high-resolution optical microscope is used as the observation device to observe and identify microorganisms, it can be preliminarily determined whether a single colony is a target microorganism required by researchers or whether a colony is a single colony. In addition, the observation device is used for photographing a formation process (such as color, shape, and size) of a single colony under high pressure to facilitate subsequent selection of the single colony.

The environmental parameter detection unit includes a temperature sensor and a pressure sensor. The temperature sensor and the pressure sensor are both arranged in the separation operation incubator, and used for detecting temperature and pressure changes in the separation operation incubator in real time and transmitting data to the central control system.

In the above-mentioned solution, the temperature sensor and the pressure sensor are both arranged on the inner edge of the cover, and mainly used for monitoring the temperature and pressure changes in the separation operation incubator, so that macro-control of the entire culture environment during practical application is facilitated.

The pressure control unit includes an air compressor, a booster pump, a gas storage tank, a pressure regulating valve, a gas inlet valve, and a gas supply pipeline. The air compressor, the booster pump, the gas storage tank, and the pressure regulating valve are connected in sequence through the gas supply pipeline, and finally connected to the separation operation incubator through the gas inlet valve. A control end of the air compressor, a control end of the booster pump, a control end of the pressure regulating valve, and a control end of the gas inlet valve are all electrically connected to the central control system.

In the above-mentioned solution, the pressure control unit is mainly used for injecting a gas into the separation operation incubator to boost pressure.

A water jacket device wrapped on an outer wall of the separation operation incubator is used as the temperature control unit, and a control end of the water jacket device is electrically connected to the central control system.

The liquid injection unit includes a microbial enrichment kettle, a liquid supply pipeline, and a microbial injection pump. The microbial enrichment kettle is used for enriching a microbial bacteria liquid, and an output end of the microbial enrichment kettle is connected to the separation operation incubator through the liquid supply pipeline. The microbial injection pump is arranged on the liquid supply pipeline, and a control end of the microbial injection pump is electrically connected to the central control system.

The liquid injection unit further includes a groove formed in an inner bottom surface of the cover of the separation operation incubator. A liquid outlet of the liquid supply pipeline in the separation operation incubator is arranged in the groove.

In the above-mentioned solution, the groove is mainly used for holding a microbial bacteria liquid injected by the microbial injection pump, so that the microbial bacteria liquid cannot flow freely after being injected into the separation operation incubator, and the realization of subsequent separation and streaking operations is ensured.

The liquid injection unit further includes a discharge valve arranged on the liquid supply pipeline, and a control end of the discharge valve is electrically connected to the central control system.

In the above-mentioned solution, when an excess bacteria liquid is remained after the sampling probe device streaks on the culture medium, the excess bacteria liquid can be slowly discharged through the discharge valve to prevent the excess bacteria liquid from flowing into the culture medium in the base.

The sampling unit includes a reaction kettle, a sampling pipeline, and a sampling valve. The reaction kettle is connected to the separation operation incubator through the sampling pipeline. The sampling valve is arranged on the sampling pipeline, and a control end of the sampling valve is electrically connected to the central control system.

In the above-mentioned solution, the inner diameter of the sampling pipeline and the sampling valve is greater than the diameter of the sampling probe device, mainly to ensure that the sampling probe device can be extended into the sampling pipeline to transfer a dipped single colony to the reaction kettle containing a liquid culture medium under pressure-holding conditions. In order to facilitate the transfer without cross-contamination, after a single colony is transferred, the sampling valve can be closed, and the reaction kettle can be replaced with a next one. At this time, 75% alcohol is contained in the reaction kettle. After the sampling probe device is completely disinfected, a next reaction kettle containing a liquid culture medium is used. On this basis, the separation and culture of the single colony in a pressure-holding state can be completed. A pressure difference that occurs when the reaction kettle is replaced every time can be controlled by the pressure control unit and pressure can be supplemented by the pressure control unit.

The present invention further provides a method for separating a single colony in a deep-sea in-situ environment. The method is realized by using the device for separating a single colony in a deep-sea in-situ environment as described above, and specifically includes the following steps:

S1: cleaning and sterilizing the device for separating a single colony in a deep-sea in-situ environment, and loading the device into a culture medium;

S2: injecting a gas into the separation operation incubator through the pressure control unit, so that a pressure value in the separation operation incubator is consistent with that of a microbial enrichment environment;

S3: activating the temperature control unit, so that the temperature of the separation operation incubator is consistent with that of the microbial enrichment environment;

S4: injecting a microbial bacterial liquid into the separation operation incubator through the liquid injection unit, controlling the sampling probe device to slide on the inner slide rail to dip the microbial bacteria liquid first, and then making the sampling probe device to be located on the surface of the culture medium to carry out streaking on the surface of the culture medium according to a certain trajectory;

S5: making separated microorganisms grow according to the streaked trajectory, and observing the microorganisms in real time through the observation area;

S6: when a single colony is formed on the culture medium, activating the sampling unit, so that the temperature and pressure of the sampling unit are consistent with those of the separation operation incubator; and S7: controlling the sampling probe device to select a single colony on the culture medium and transfer the single colony to the sampling unit containing a liquid culture medium to realize transfer and culture of a single colony under pressure-holding conditions.

In the above-mentioned solution, a high-pressure environment in the isolation operation incubator 2 is mainly constructed, which is the same as the marine environment where microorganisms live in. First, the separation operation incubator is cleaned, and the cover and the base are opened and separately wiped with 75% alcohol. After the alcohol is completely evaporated, the separation operation incubator is sterilized under an ultraviolet light for 15 minutes. After the sterilization is completed, a previously sterilized solid culture medium is added into the base, and the cover is closed. Next, a pressure value in the separation operation incubator is determined according to a pressure value in the microbial enrichment kettle. A gas is injected into the separation operation incubator through the pressure control unit, so that the pressure value in the separation operation incubator is consistent with that in the microbial enrichment kettle.

Next, a temperature value in the separation operation incubator is determined according to a temperature value in the microbial enrichment kettle. The separation operation incubator is put in a water bath environment of the water jacket device, so that the temperature is consistent with that in the microbial enrichment kettle. Next, the observation device is adjusted, so that situations on the culture medium in the base can be clearly observed. Then, a bacteria liquid containing microorganisms is injected into the groove from the microbial enrichment kettle through the microbial injection pump, so that droplets formed by the bacteria liquid are located in the groove. The sampling probe device is controlled to dip the bacteria liquid in the groove. Then, the bottom of the sampling probe device is made to be located on the surface of the culture medium, so as to make the sampling probe device carry out streaking on the surface of the culture medium according to a certain trajectory. At last, separated microorganisms grow according to the streaked trajectory to achieve separation of a single colony. The whole process is observed through the visible window on the cover. When a single colony is formed on the culture medium, the streaking operation can be carried out.

Before a single colony is separated, the tail end of the sampling pipeline is connected to the reaction kettle first, and the sampling valve is opened, 75% alcohol is contained in the reaction kettle. Then, the pressure of the whole device is maintained constant through the pressure control unit. At last, the sampling probe device is controlled by the central control system to pass through the sampling pipeline and enter the reaction kettle, so that sterilizing process of the sampling probe device is achieved. Moreover, the sampling valve is closed, and the reaction kettle containing 75% alcohol is replaced with a reaction kettle containing a liquid culture medium. Then, the pressure of the whole device is maintained constant through the pressure control unit. At last, the sampling probe device is controlled by the central control system to successfully select a single colony on the culture medium, and to make pass through the sampling pipeline and the reaction kettle containing a liquid culture medium. Finally, the transfer and culture of a single colony under pressure-holding conditions are achieved. Subsequent single colonies can be separated in a similar fashion. In the whole selection and culture processes, the pressure and temperature values in the separation operation incubator are maintained consistent with the pressure and temperature environment in a high-pressure enrichment system where the microorganisms are originally located, so that the microorganisms are separated under in-situ high pressure conditions.

According to the above-mentioned solutions, in view of the problem of difficult separation of marine microorganisms, the device and method for separating a single colony in a high pressure environment are provided. Compared with existing separation and culture under normal pressure, the device and method have the advantages that requirements of enrichment, separation and culture of microorganisms in a deep-sea in-situ high pressure environment can be met, and the problems are solved that deep-sea in-situ barophilic bacteria cannot survive after culture in a normal pressure environment or have different expressions. Compared with existing enrichment, separation, and culture under high pressure, the device and method have the advantages that a single colony can be selected and successfully cultured under pressure-holding conditions.

Compared with the prior art, the technical solutions of the present invention have the following beneficial effects.

The present invention provides a device and method for separating a single colony in a deep-sea in-situ environment. A single colony is separated, selected, and cultured under pressure-holding conditions by establishing a single colony separation device. At last, a target bacterium can be obtained. The cultivability of marine microorganisms is effectively improved, and a basic device and method are provided for separation and culture of the marine microorganisms.

and callouts in the figures are as follows: 1, central control system; 2, separation operation incubator; 21, base; 211, culture area; 22, cover; 221, observation area; 2211, outer slide rail; 2212, connection bracket; 2213, observation device; 2214, visible window; 222, separation operation area; 2221, inner slide rail; 2222, sampling probe device; 3, environmental parameter detection unit; 31, temperature sensor; 32, pressure sensor; 4, pressure control unit; 41, air compressor; 42, booster pump; 43, gas storage tank; 44, pressure regulating valve; 45, gas inlet valve; 46, gas supply pipeline; 5, temperature control unit; 6, liquid injection unit; 61, microbial enrichment kettle; 62, liquid supply pipeline; 63, microbial injection pump; 64, groove; 65, discharge valve; 7, sampling unit; 71, reaction kettle; 72, sampling pipeline; and 73, sampling valve.

DETAILED DESCRIPTION

The accompanying drawings are merely used for illustrating the present invention, and should not be construed as limitations on this patent.

The following examples are complete use examples with rich contents.

In order to better illustrate the embodiments, some parts in the accompanying drawings are omitted, enlarged, or reduced, and do not represent the size of actual products.

It may be understood by those skilled in the art that some well-known structures in the accompanying drawings and descriptions thereof may be omitted.

The technical solutions of the present invention are further described below in conjunction with the accompanying drawings and embodiments.

Embodiment 1

Figure 1:
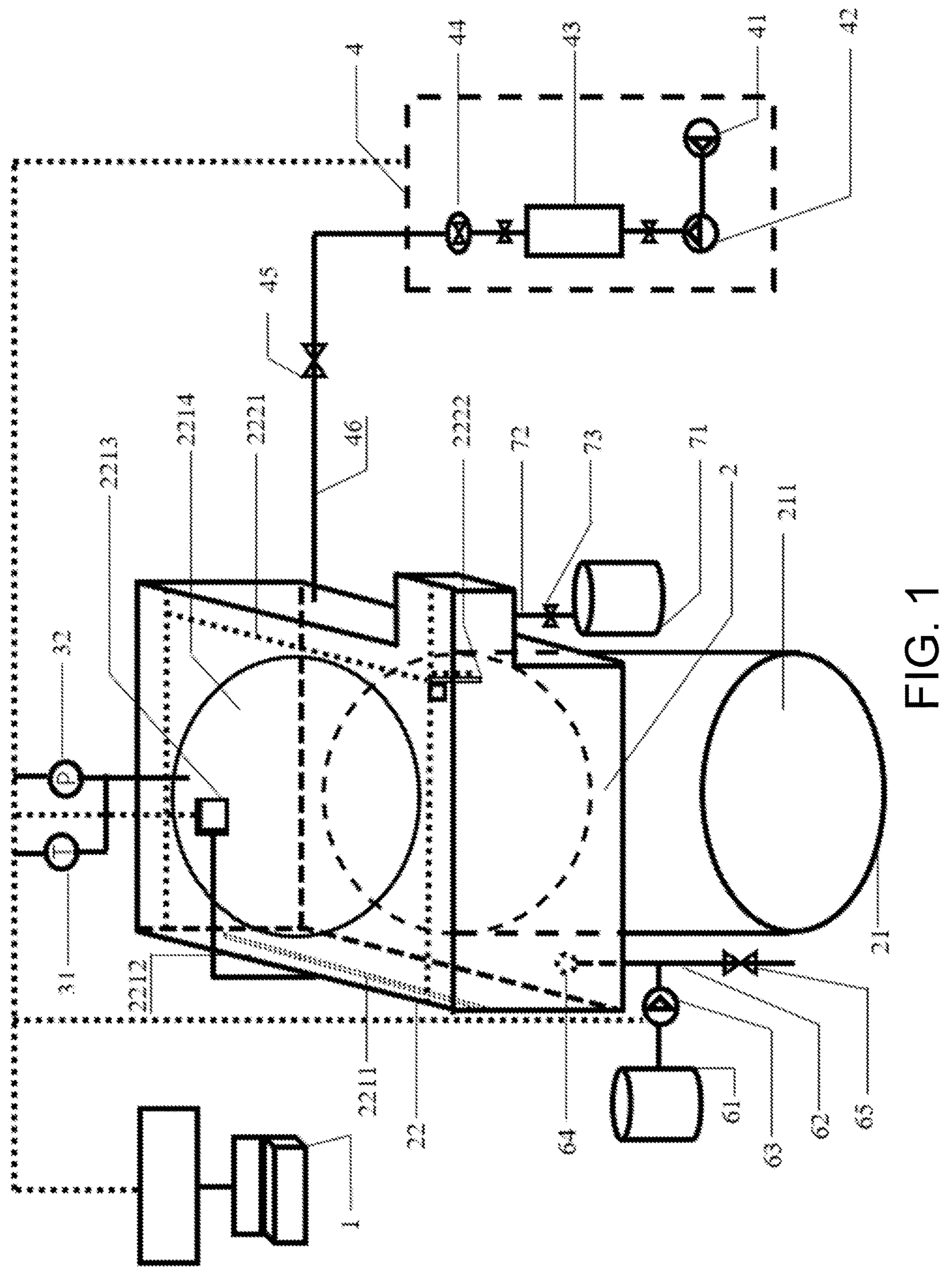
FIG. 1 is a schematic structural diagram of a device in the present invention.
Figure 2:
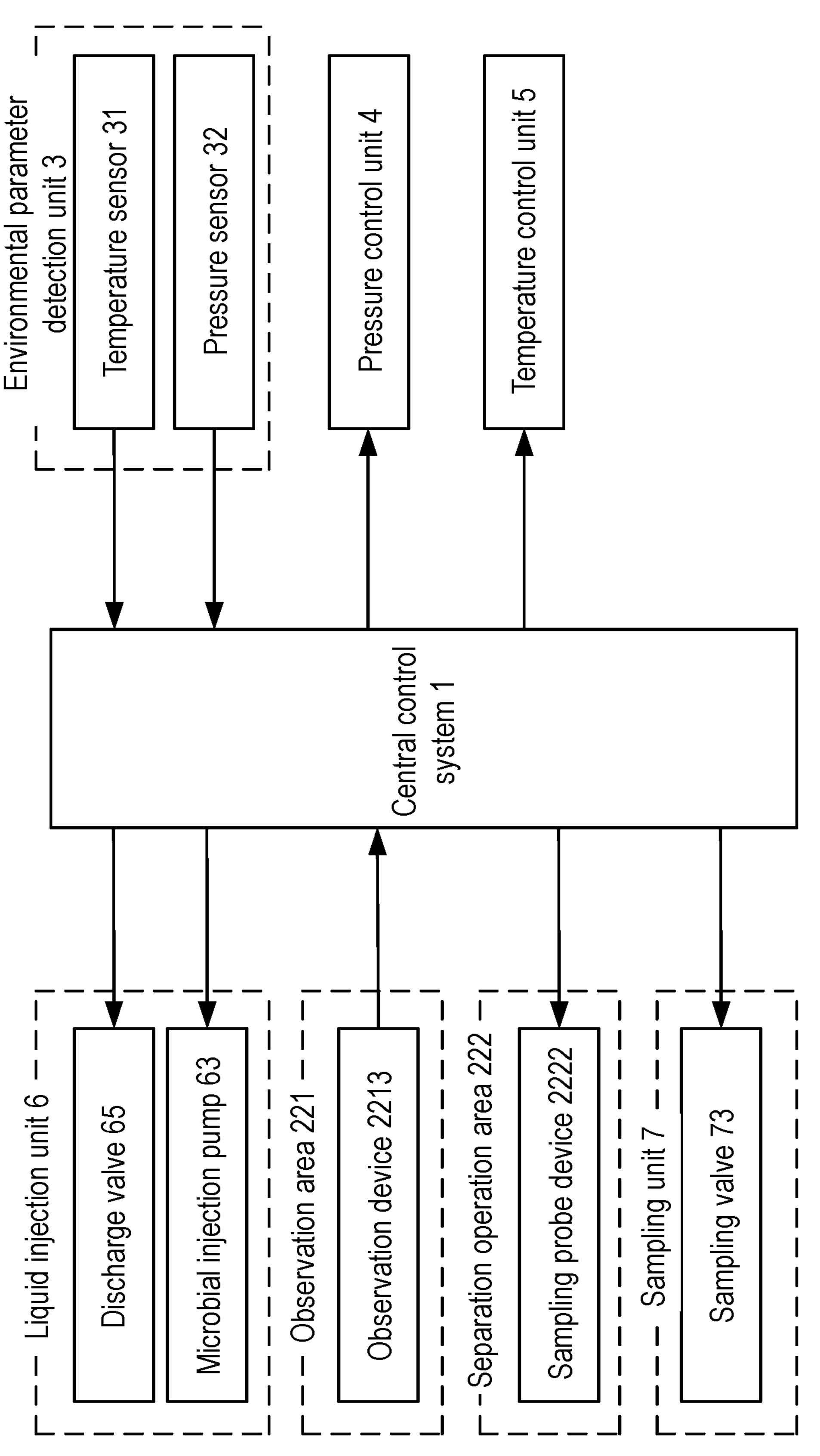
FIG. 2 is a schematic diagram showing connection of circuit modules of a central control system in the present invention.

As shown in FIG. 1 and FIG. 2, this embodiment provides a device for separating a single colony in a deep-sea in-situ environment. The device includes a central control system 1, a separation operation incubator 2, an environmental parameter detection unit 3, a pressure control unit 4, a temperature control unit 5, a liquid injection unit 6, and a sampling unit 7. The separation operation incubator 2 includes a base 21, and a cover 22 fixedly connected to the base 21. The cover 22 is used as an observation area 221 and a separation operation area 222, and the base 21 is used as a culture area 211. The observation area 21 is used for observation of separation and culture processes. An inner slide rail 2221 is arranged in the separation operation area 222 according to separation operation needs. A sampling probe device 2222 capable of sliding on the inner slide rail 2221 is installed on the inner slide rail 2221, and used for carrying out a streaking operation and a sampling operation on microorganisms. A culture medium is arranged in the culture area 211, and used for culturing streaked microbial colonies. The environmental parameter detection unit 3 is arranged in the separation operation incubator 2, and used for detecting temperature and pressure changes in the separation operation incubator 2 in real time and transmitting data to the central control system 1. The pressure control unit 4 and the temperature control unit 5 are respectively connected to the separation operation incubator 2 to ensure that the pressure and temperature in the separation operation incubator 2 are consistent with a growth and culture environment of microorganisms. The liquid injection unit 6 is used for injecting an enriched microbial bacteria liquid into the separation operation incubator 2 to achieve dipping and streaking by the sampling probe device 2222. The sampling unit 7 is used for carrying out pressure-holding sampling on microorganisms. A control end of the sampling probe device 2222, a control end of the pressure control unit 4, a control end of the temperature control unit 5, a control end of the liquid injection unit 6, and a control end of the sampling unit 7 are all electrically connected to the central control system 1. A data output end of the observation area 221 is electrically connected to the central control system 1.

In a specific implementation process, the base 21 and the cover 22 are sealed and connected by a buckle. The base similar to a cylinder, the cover has a shape similar to that of an "L". The inner slide rail 2221 is a three-dimensional slide rail. The sampling probe device 2222 can slide up, down, left, and right on the inner slide rail 2221, mainly to ensure that the sampling probe device 2222 can contact the surface of the culture medium in the base 21, and also be located above the culture medium in the base 21, so that convenience is provided for the sampling probe device 2222 to carry out various operations on the culture medium. The sampling probe device 2222 is mainly controlled by using the central control system 1 to control a pressure-holding chip of the sampling probe device 2222 and to control the sampling probe device to be displayed.

In a specific implementation process, the central control system 1 includes a server, a computer, and the like, and is used for realizing recording of changes in various environmental data information of enriched marine microorganisms during separation and culture in a high pressure environment, and for realizing real-time acquisition, the data information, processing, storage, and image output.

More specifically, the observation area 221 includes an outer slide rail 2211 arranged on an outer side surface of the cover 22, a connection bracket 2212 slidably connected to the outer slide rail 2211, an observation device 2213 fixed to an end of the connection bracket 2212, and a visible window 2214 arranged on a surface of the cover 22. A data output end of the observation device 2213 is electrically connected to the central control system 1.

In a specific implementation process, the visible window 2214 is a circular visible window arranged in the center of the cover 22, so that convenience is provided for the observation device 2213 to observe the inside of the separation operation incubator 2. The outer slide rail 2211 is a horizontal slide rail, the telescopic L-shaped connection bracket 2212 is installed on the slide rail, and the observation device 2213 is arranged at the end of the connection bracket 2212 to facilitate observation and identification of microorganisms. For example, when an optical observation module of a high-resolution optical microscope is used as the observation device 2213 to observe and identify microorganisms, it can be preliminarily determined whether a single colony is a target microorganism required by researchers or whether a colony is a single colony. In addition, the observation device is used for photographing a formation process (such as color, shape, and size) of a single colony under high pressure to facilitate subsequent selection of the single colony.

More specifically, the environmental parameter detection unit 3 includes a temperature sensor 31 and a pressure sensor 32. The temperature sensor 31 and the pressure sensor 32 are both arranged in the separation operation incubator 2, and used for detecting temperature and pressure changes in the separation operation incubator 2 in real time and transmitting data to the central control system 1.

In a specific implementation process, the temperature sensor 31 and the pressure sensor 32 are both arranged on the inner edge of the cover 22, and mainly used for monitoring the temperature and pressure changes in the separation operation incubator 2, so that macro-control of the entire culture environment during practical application is facilitated.

More specifically, the pressure control unit 4 includes an air compressor 41, a booster pump 42, a gas storage tank 43, a pressure regulating valve 44, a gas inlet valve 45, and a gas supply pipeline 46. The air compressor 41, the booster pump 42, the gas storage tank 43, and the pressure regulating valve 44 are connected in sequence through the gas supply pipeline 46, and finally connected to the separation operation incubator 2 through the gas inlet valve 45. A control end of the air compressor 41, a control end of the booster pump 42, a control end of the pressure regulating valve 44, and a control end of the gas inlet valve 45 are all electrically connected to the central control system 1.

In a specific implementation process, the pressure control unit 4 is mainly used for injecting a gas into the separation operation incubator 2 to boost pressure.

More specifically, a water jacket device wrapped on an outer wall of the separation operation incubator 2 is used as the temperature control unit 5, and a control end of the water jacket device is electrically connected to the central control system 1.

More specifically, the liquid injection unit 6 includes a microbial enrichment kettle 61, a liquid supply pipeline 62, and a microbial injection pump 63. The microbial enrichment kettle 61 is used for enriching a microbial bacteria liquid, and an output end of the microbial enrichment kettle is connected to the separation operation incubator 2 through the liquid supply pipeline 62. The microbial injection pump 63 is arranged on the liquid supply pipeline 62, and a control end of the microbial injection pump is electrically connected to the central control system 1.

More specifically, the liquid injection unit 6 further includes a groove 64 formed in an inner bottom surface of the cover 22 of the separation operation incubator 2. A liquid outlet of the liquid supply pipeline 62 in the separation operation incubator 2 is arranged in the groove 64.

In a specific implementation process, the groove 64 is mainly used for holding a microbial bacteria liquid injected by the microbial injection pump 63, so that the microbial bacteria liquid cannot flow freely after being injected into the separation operation incubator 2, and the realization of subsequent separation and streaking operations is ensured.

More specifically, the liquid injection unit 6 further includes a discharge valve 65 arranged on the liquid supply pipeline 62, and a control end of the discharge valve 65 is electrically connected to the central control system 1.

In a specific implementation process, when an excess bacteria liquid is remained after the sampling probe device 2222 streaks on the culture medium, the excess bacteria liquid can be slowly discharged through the discharge valve 65 to prevent the excess bacteria liquid from flowing into the culture medium in the base 21.

More specifically, the sampling unit 7 includes a reaction kettle 71, a sampling pipeline 72, and a sampling valve 73. The reaction kettle 71 is connected to the separation operation incubator 2 through the sampling pipeline 72. The sampling valve 73 is arranged on the sampling pipeline 72, and a control end of the sampling valve is electrically connected to the central control system 1.

In a specific implementation process, the inner diameter of the sampling pipeline 72 and the sampling valve 73 is greater than the diameter of the sampling probe device 2222, mainly to ensure that the sampling probe device 2222 can be extended into the sampling pipeline 72 to transfer a dipped single colony to the reaction kettle 71 containing a liquid culture medium under pressure-holding conditions. In order to facilitate the transfer without cross-contamination, after a single colony is transferred, the sampling valve 73 can be closed, and the reaction kettle 71 can be replaced with a next one. At this time, 75% alcohol is contained in the reaction kettle 71. After the sampling probe device 2222 is completely disinfected, a next reaction kettle 71 containing a liquid culture medium is used. And so on in a similar fashion, the separation and culture of the single colony in a pressure-holding state can be completed. A pressure difference that occurs when the reaction kettle 71 is replaced every time can be controlled by the pressure control unit 4 and pressure can be supplemented by the pressure control unit 4.

In a specific implementation process of this embodiment, a single colony is separated, selected, and cultured under pressure-holding conditions by establishing a single colony separation device. At last, a target bacterium can be obtained. The cultivability of marine microorganisms is effectively improved, and a basic solution is provided for separation and culture of the marine microorganisms. According to the above-mentioned solution, the enriched marine microorganisms can be separated under pressure-holding conditions in an in-situ high pressure environment, so that requirements of subsequent culture, functional identification, and the like are met.

Embodiment 2

Figure 3:
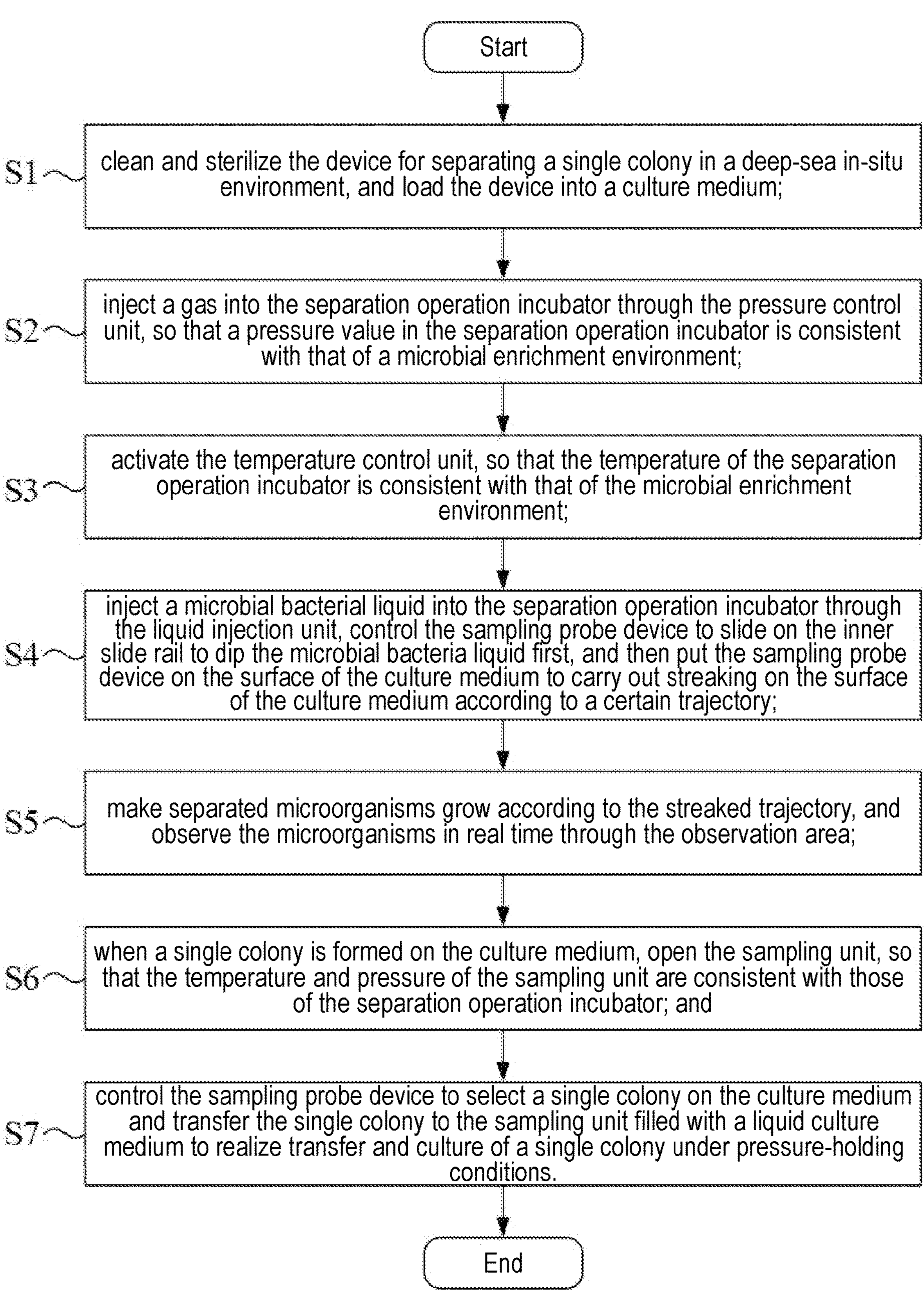
FIG. 3 is a schematic flow chart of a method in the present invention.

More specifically, on the basis of embodiment 1 and as shown in FIG. 3, this embodiment provides a method for separating a single colony in a deep-sea in-situ environment. The method is realized by using the device for separating the single colony in the deep-sea in-situ environment, and specifically includes the following steps:

S1: cleaning and sterilizing the device for separating the single colony in the deep-sea in-situ environment, and loading the device into a culture medium;

S2: injecting a gas into the separation operation incubator 2 through the pressure control unit 4, so that a pressure value in the separation operation incubator 2 is consistent with that of a microbial enrichment environment;

S3: activating the temperature control unit 5, so that the temperature of the separation operation incubator 2 is consistent with that of the microbial enrichment environment;

S4: injecting a microbial bacterial liquid into the separation operation incubator 2 through the liquid injection unit 6, controlling the sampling probe device 2222 to slide on the inner slide rail 2221 to dip the microbial bacteria liquid first, and then making the sampling probe device 2222 to be on the surface of the culture medium to carry out streaking on the surface of the culture medium according to a certain trajectory;

S5: making separated microorganisms grow according to the streaked trajectory, and observing the microorganisms in real time through the observation area 221;

S6: when a single colony is formed on the culture medium, activating the sampling unit 7, so that a temperature and a pressure of the sampling unit are consistent with those of the separation operation incubator 2; and S7: controlling the sampling probe device 2222 to select a single colony on the culture medium and transfer the single colony to the sampling unit 7 containing a liquid culture medium to realize transfer and culture of a single colony under pressure-holding conditions.

This embodiment is mainly to construct a high-pressure environment in the isolation operation incubator 2, which is the same as the marine environment where microorganisms lives in. First, the separation operation incubator 2 is cleaned, and the cover 22 and the base 21 are opened and separately wiped with 75% alcohol. After the alcohol is completely evaporated, the separation operation incubator is sterilized under an ultraviolet light for 15 minutes. After the sterilization is completed, a previously sterilized solid culture medium is added into the base 21, and the cover 22 is closed. Next, a pressure value in the separation operation incubator 2 is determined according to a pressure value in the microbial enrichment kettle 61. A gas is injected into the separation operation incubator 2 through the pressure control unit 4, so that the pressure value in the separation operation incubator 2 is consistent with that in the microbial enrichment kettle 61.

Next, a temperature value in the separation operation incubator 2 is determined according to a temperature value in the microbial enrichment kettle 61. The separation operation incubator 2 is put in a water bath environment of the water jacket device, so that the temperature is consistent with that in the microbial enrichment kettle 61. Next, the observation device 2213 is adjusted, so that situations on the culture medium in the base 21 can be clearly observed. Then, a bacteria liquid containing microorganisms is injected into the groove 64 through the microbial injection pump 63 from the microbial enrichment kettle 61, so that droplets formed by the bacteria liquid are contained in the groove 64. The sampling probe device 2222 is controlled to dip the bacteria liquid in the groove 64. Then, the bottom of the sampling probe device 2222 is made to be located on the surface of the culture medium, so as to make the sampling probe device 2222 carry out streaking on the surface of the culture medium according to a certain trajectory. At last, separated microorganisms grow according to the streaked trajectory to achieve separation of a single colony. The whole process is observed through the visible window 2214 on the cover 22. When a single colony is formed on the culture medium, the streaking operation can be carried out.

Before a single colony is separated, the tail end of the sampling pipeline 72 is connected to the reaction kettle 71 first, and the sampling valve 73 is opened, 75% alcohol in contained in the reaction kettle 71. Then, the pressure of the whole device is maintained constant through the pressure control unit 4. At last, the sampling probe device 2222 is controlled by the central control system 1 to enter the reaction kettle 71 through the sampling pipeline 72, so that sterilizing process of the sampling probe device 2222 is achieved. Moreover, the sampling valve 73 is closed, and the reaction kettle 71 containing 75% alcohol is replaced with a reaction kettle 71 containing a liquid culture medium. Then, the pressure of the whole device is maintained constant through the pressure control unit 4. At last, the sampling probe device 2222 is controlled by the central control system 1 to successfully select a single colony on the culture medium, and to pass through the sampling pipeline 72 and enter the reaction kettle 71 containing a liquid culture medium. Finally, the transfer and culture of a single colony under pressure-holding conditions are achieved. Subsequent single colonies can be separated in a similar fashion. In the whole selection and culture processes, the pressure and temperature values in the separation operation incubator 2 are maintained consistent with the pressure and temperature environment in a high-pressure enrichment system where the microorganisms are originally located, so that the microorganisms are separated under in-situ high pressure conditions.

According to this embodiment, in view of the problem of difficult separation of marine microorganisms, the device and method for separating a single colony in a high pressure environment are provided. Compared with existing separation and culture under normal pressure, the device and method have the advantages that requirements of enrichment, separation and culture of microorganisms in a deep-sea in-situ high pressure environment can be met, and the problems are solved that deep-sea in-situ barophilic bacteria cannot survive after culture in a normal pressure environment or have different expressions. Compared with existing enrichment, separation, and culture under high pressure, the device and method have the advantages that a single colony can be selected and successfully cultured under pressure-holding conditions.

Embodiment 3

In order to further illustrate the technical realization process and technical effects of the present invention, this embodiment provides separation and culture of enriched deep-sea methanotrophs in an in-situ high pressure environment. Requirements of subsequent works such as library construction and functional identification are met. An operation technology for separating a single colony is the core of this embodiment, and other parts of this embodiment mainly include a pressure control unit 4, a separation operation incubator 2, and a central control system 1.

The separation operation incubator 2 mainly includes a cover 22 and a base 21. The base 21 and the cover 22 are connected by a buckle. The base similar to a cylinder, the cover has a shape similar to that of an "L". A temperature sensor 31 and a pressure sensor 32 are arranged on the inner edge of the cover 22, and mainly used for monitoring temperature and pressure changes in the separation operation incubator 2. A circular visible window 2214 is arranged in the middle of the upper part of the cover 22, and mainly used for using of an observation device 2213. A three-dimensional inner slide rail 2221 is arranged in the cover 22, mainly to ensure that a sampling probe device 2222 can contact the surface of the culture medium in the base 21, and also be located above the culture medium in the base 21, so that convenience is provided for the sampling probe device 2222 to carry out various operations on the surface of the culture medium. The operations are mainly carried out by using central control system 1 to control a pressure-holding chip of the sampling probe device 2222 and carrying out display on a computer. A horizontal outer slide rail 2211 is arranged on an outer wall of the left side of the cover 22, a telescopic L-shaped connection bracket 2212 is installed on the outer slide rail 2211, and the observation device 2213 is arranged at the other end of the L-shaped connection bracket 2212. For example, when an optical observation module of a high-resolution optical microscope is used for observing and identifying microorganisms, it can be preliminarily determined whether a single colony is a target microorganism required by researchers or whether a colony is a single colony. In addition, the optical observation module is used for photographing a formation process (such as color, shape, and size) of a single colony under high pressure to facilitate subsequent selection of the single colony.

A groove 64 is formed in the lower left part of the cover 22, and mainly used for holding a microbial bacteria liquid injected by a microbial injection pump 63. When an excess bacteria liquid is remained after the sampling probe device 2222 streaks on the culture medium, the excess bacteria liquid can be slowly discharged through a discharge valve 65 to prevent the excess bacteria liquid from flowing into the culture medium in the base 21. The bottom of the right rear part of the cover 22 is provided with a sampling pipeline 72. The inner diameter of the sampling pipeline 72 and a sampling valve 73 is greater than the diameter of the sampling probe device 2222, mainly to ensure that the sampling probe device 2222 can be extended into the sampling pipeline 72 to transfer a dipped single colony to a reaction kettle 71 containing a liquid culture medium under pressure-holding conditions. In order to facilitate the transfer without cross-contamination, the sampling pipeline 72 is provided with the sampling valve 73. After a single colony is transferred, the sampling valve 73 can be closed, and the reaction kettle 71 can be replaced with a next reaction kettle 71. At this time, 75% alcohol is contained in the next reaction kettle 71. After the sampling probe device 2222 is completely disinfected, a next reaction kettle 71 containing a liquid culture medium is used. The rest can be proceeded in a similar fashion to complete the separation and culture of the single colony in a pressure-holding state. A pressure difference that occurs when the reaction kettle 71 is replaced every time can be controlled by the pressure control unit 4 and corresponding pressure supplemented by the pressure control unit 4.

The pressure control unit 4 involved in this embodiment mainly used for injecting a gas into a culture kettle to boost pressure, and includes a gas storage tank 43, a pressure regulating valve 44, an air compressor 41, and a booster pump 42. The central control system 1 involved in this embodiment includes a server, a computer, and the like, and is used for realizing recording of real-time acquisition, processing, storage, and image output of changes in various environmental data information of enriched marine microorganisms during separation and culture in a high pressure environment and for realizing real-time acquisition, the data information, processing, storage, and image output.

According to a device and technology for separating and culturing a single colony of marine microorganisms under high pressure involved in this embodiment, a high-pressure environment same mainly constructed in the separation operation incubator 2, which is the same as the marine environment where methanotrophs live in. First, the separation operation incubator 2 is cleaned, and the cover 22 and the base 21 are opened and respectively wiped with 75% alcohol. After the alcohol is completely evaporated, the separation operation incubator is sterilized under an ultraviolet light for 15 minutes. After the sterilization is completed, a previously sterilized solid culture medium is added into the base 21, and the cover 22 is closed. Next, a pressure value in a culture dish is determined according to a pressure value in a microbial enrichment kettle 61. A methane gas is injected into the separation operation incubator 2 through the pressure control unit 4, so that the pressure value in the separation operation incubator 2 is consistent with that in the microbial enrichment kettle 61.

Next, a temperature value in the separation operation incubator 2 is determined according to a temperature value in the microbial enrichment kettle 61. The separation operation incubator 2 is put in a water bath environment, so that the temperature is consistent with that in the microbial enrichment kettle 61. Next, the observation device 2213 is adjusted, so that situations on the culture medium in the base 21 can be clearly observed. Then, a bacteria liquid containing microorganisms is injected into the groove 64 through the microbial injection pump 63 from the microbial enrichment kettle 61, so that droplets formed by the bacteria liquid are contained in the groove 64. The sampling probe device 2222 is controlled to dip the bacteria liquid in the groove 64. Then, the bottom of the sampling probe device 2222 is made to be located on the surface of the culture medium, so as to make the sampling probe device 2222 carry out streaking on the surface of the culture medium according to a certain trajectory. At last, separated microorganisms grow according to the streaked trajectory to achieve separation of a single colony. The visible window 2214 on the cover 22 is used for observation. When a single colony is formed on the culture medium, the streaking operation can be carried out. Before a single colony is separated, the tail end of the sampling pipeline 72 is connected to the reaction kettle 71 first, and the sampling valve 73 is opened, 75% alcohol is contained in the reaction kettle 71. Then, the pressure of the whole device is maintained constant through the pressure control unit 4. At last, the sampling probe device 2222 is controlled by the central control system 1 to enter the reaction kettle 71 through the sampling pipeline 72, so that the sampling probe device 2222 is sterilized. Moreover, the sampling valve 73 is closed, and the reaction kettle 71 containing alcohol is replaced with a reaction kettle 71 containing a liquid culture medium. Then, the pressure of the whole device is maintained constant through the pressure control unit 4. At last, the sampling probe device 2222 is controlled by the central control system 1 to successfully select a single colony on the culture medium, and to pass through the sampling pipeline 72 and enter the reaction kettle 71 containing a liquid culture medium. Finally, the transfer and culture of a single colony under pressure-holding conditions are achieved. Subsequent single colonies can be separated in a similar fashion. In the whole selection and culture processes, the pressure and temperature values in the incubator are maintained consistent with the pressure and temperature environment in the microbial enrichment kettle 61 where the microorganisms are originally located, so that the microorganisms are separated under in-situ high pressure conditions.

In a specific implementation process, according to the device and technology for separating and culturing marine microorganisms in a high pressure environment provided in this embodiment, the formation and culture of a single colony of microorganisms in a marine high pressure environment can be achieved, and demands for growth and culture of special deep-sea bacteria are met. Compared with current traditional technologies for enrichment and separation of marine microorganisms in a normal pressure environment, the problems that marine baroduric bacteria and barophilic bacteria have low survival rates in the normal pressure environment, that deep-sea indigenous characteristics cannot be effectively expressed in the normal pressure environment, that current marine microorganisms have low culture degrees, that pure bacteria are difficult to culture, can be effectively solved. According to this embodiment, the processes of separating, selecting, and culturing a single colony artificially in a high pressure environment can be achieved. Compared with conventional technologies for separation and culture of microorganisms, the culture efficiency and purification efficiency of the microorganisms are effectively improved in this embodiment.

Apparently, the above-mentioned embodiment s of the present invention are merely examples to clearly illustrate the present invention, rather than to limit the implementations of the present invention. Changes or modifications in other different forms can also be made by those of ordinary skill in the art on the basis of the above description. Herein, it is unnecessary and impossible to illustrate all the embodiments. Any modifications, equivalent replacements, improvements, and the like made within the spirit and principle of the present invention shall be included within the protection scope of the claims of the present invention.

What is claimed is:

1. A device for separating a single colony in a deep-sea in-situ environment, comprising a central control system, a separation operation incubator, an environmental parameter detection unit, a pressure control unit, a temperature control unit, a liquid injection unit, and a sampling unit, wherein the environmental parameter detection unit comprises a temperature sensor and a pressure sensor, the separation operation incubator comprises a base, and a cover fixedly connected to the base; the cover is used as an observation area and a separation operation area, and the base is used as a culture area; the observation area is used for observation of separation and culture processes; an inner slide rail is arranged in the separation operation area according to separation operation needs, and a sampling probe device capable of sliding on the inner slide rail is installed on the inner slide rail, and used for carrying out a streaking operation and a sampling operation on microorganisms; a culture medium is arranged in the culture area, and used for culturing streaked microbial colonies;

the environmental parameter detection unit is arranged in the separation operation incubator, and used for detecting temperature and pressure changes in the separation operation incubator in real time and transmitting data to the central control system;

the pressure control unit and the temperature control unit are respectively connected to the separation operation incubator to ensure that a pressure and a temperature in the separation operation incubator are consistent with a growth and culture environment of microorganisms;

the liquid injection unit is used for injecting an enriched microbial bacteria liquid into the separation operation incubator to achieve dipping and streaking by the sampling probe device;

the sampling unit is used for carrying out pressure-holding sampling on microorganisms;

a control end of the sampling probe device, a control end of the pressure control unit, a control end of the temperature control unit, a control end of the liquid injection unit, and a control end of the sampling unit are all electrically connected to the central control system, the observation area comprises an outer slide rail arranged on an outer side surface of the cover, a connection bracket slidably connected to the outer slide rail, an observation device fixed to an end of the connection bracket, and a visible window arranged on a surface of the cover; and a data output end of the observation device of the observation area is electrically connected to the central control system.

2. The device for separating the single colony in the deep-sea in-situ environment according to claim 1, wherein the temperature sensor and the pressure sensor are both arranged in the separation operation incubator, and used for detecting temperature and pressure changes in the separation operation incubator in real time and transmitting data to the central control system.

3. The device for separating the single colony in the deep-sea in-situ environment according to claim 1, wherein the pressure control unit comprises an air compressor, a booster pump, a gas storage tank, a pressure regulating valve, a gas inlet valve, and a gas supply pipeline;

the air compressor, the booster pump, the gas storage tank, and the pressure regulating valve are connected in sequence through the gas supply pipeline, and finally connected to the separation operation incubator through the gas inlet valve; and a control end of the air compressor, a control end of the booster pump, a control end of the pressure regulating valve, and a control end of the gas inlet valve are all electrically connected to the central control system.

4. The device for separating the single colony in the deep-sea in-situ environment according to claim 1, wherein a water jacket device wrapped on an outer wall of the separation operation incubator is used as the temperature control unit, and a control end of the water jacket device is electrically connected to the central control system.

5. The device for separating the single colony in the deep-sea in-situ environment according to claim 1, wherein the liquid injection unit comprises a microbial enrichment kettle, a liquid supply pipeline, and a microbial injection pump;

the microbial enrichment kettle is used for enriching a microbial bacteria liquid, and an output end of the microbial enrichment kettle is connected to the separation operation incubator through the liquid supply pipeline; and the microbial injection pump is arranged on the liquid supply pipeline, and a control end of the microbial injection pump is electrically connected to the central control system.

6. The device for separating the single colony in the deep-sea in-situ environment according to claim 5, wherein the liquid injection unit further comprises a groove formed in an inner bottom surface of the cover of the separation operation incubator; and a liquid outlet of the liquid supply pipeline in the separation operation incubator is arranged in the groove.

7. The device for separating the single colony in the deep-sea in-situ environment according to claim 6, wherein the liquid injection unit further comprises a discharge valve arranged on the liquid supply pipeline, and a control end of the discharge valve is electrically connected to the central control system.

8. The device for separating the single colony in the deep-sea in-situ environment according to claim 1, wherein the sampling unit comprises a reaction kettle, a sampling pipeline, and a sampling valve;

the reaction kettle is connected to the separation operation incubator through the sampling pipeline; and the sampling valve is arranged on the sampling pipeline, and a control end of the sampling valve is electrically connected to the central control system.

9. A method for separating a single colony in a deep-sea in-situ environment, the method is realized by using the device for separating the single colony in the deep-sea in-situ environment according to claim 1, and specifically comprises following steps:

S1: cleaning and sterilizing the device for separating the single colony in the deep-sea in-situ environment, and loading the device into the culture medium;

S2: injecting a gas into the separation operation incubator through the pressure control unit, so that a pressure value in the separation operation incubator is consistent with that of a microbial enrichment environment;

S3: activating the temperature control unit, so that the temperature of the separation operation incubator is consistent with that of the microbial enrichment environment;

S4: injecting a microbial bacterial liquid into the separation operation incubator through the liquid injection unit, controlling the sampling probe device to slide on the inner slide rail to dip the microbial bacteria liquid first, and then making the sampling probe device to be located on a surface of the culture medium to carry out streaking on the surface of the culture medium according to a certain trajectory;

S5: making separated microorganisms grow according to the trajectory, and observing the microorganisms in real time through the observation area;

S6: when a single colony is formed on the culture medium, activating the sampling unit, so that a temperature and a pressure of the sampling unit are consistent with those of the separation operation incubator; and S7: controlling the sampling probe device to select a single colony on the culture medium and transfer the single colony to the sampling unit containing a liquid culture medium to realize transfer and culture of a single colony under pressure-holding conditions.

10. A method for separating a single colony in a deep-sea in-situ environment, the method is realized by using the device for separating the single colony in the deep-sea in-situ environment according to claim 2, and specifically comprises following steps:

S1: cleaning and sterilizing the device for separating the single colony in the deep-sea in-situ environment, and loading the device into the culture medium;

S2: injecting a gas into the separation operation incubator through the pressure control unit, so that a pressure value in the separation operation incubator is consistent with that of a microbial enrichment environment;

S3: activating the temperature control unit, so that the temperature of the separation operation incubator is consistent with that of the microbial enrichment environment;

S4: injecting a microbial bacterial liquid into the separation operation incubator through the liquid injection unit, controlling the sampling probe device to slide on the inner slide rail to dip the microbial bacteria liquid first, and then making the sampling probe device to be located on a surface of the culture medium to carry out streaking on the surface of the culture medium according to a certain trajectory;

S5: making separated microorganisms grow according to the trajectory, and observing the microorganisms in real time through the observation area;

S6: when a single colony is formed on the culture medium, activating the sampling unit, so that a temperature and a pressure of the sampling unit are consistent with those of the separation operation incubator; and S7: controlling the sampling probe device to select a single colony on the culture medium and transfer the single colony to the sampling unit containing a liquid culture medium to realize transfer and culture of a single colony under pressure-holding conditions.

11. A method for separating a single colony in a deep-sea in-situ environment, the method is realized by using the device for separating the single colony in the deep-sea in-situ environment according to claim 3, and specifically comprises following steps:

S1: cleaning and sterilizing the device for separating the single colony in the deep-sea in-situ environment, and loading the device into the culture medium;

S2: injecting a gas into the separation operation incubator through the pressure control unit, so that a pressure value in the separation operation incubator is consistent with that of a microbial enrichment environment;

S3: activating the temperature control unit, so that the temperature of the separation operation incubator is consistent with that of the microbial enrichment environment;

S4: injecting a microbial bacterial liquid into the separation operation incubator through the liquid injection unit, controlling the sampling probe device to slide on the inner slide rail to dip the microbial bacteria liquid first, and then making the sampling probe device to be located on a surface of the culture medium to carry out streaking on the surface of the culture medium according to a certain trajectory;

S5: making separated microorganisms grow according to the trajectory, and observing the microorganisms in real time through the observation area;

S6: when a single colony is formed on the culture medium, activating the sampling unit, so that a temperature and a pressure of the sampling unit are consistent with those of the separation operation incubator; and S7: controlling the sampling probe device to select a single colony on the culture medium and transfer the single colony to the sampling unit containing a liquid culture medium to realize transfer and culture of a single colony under pressure-holding conditions.

12. A method for separating a single colony in a deep-sea in-situ environment, the method is realized by using the device for separating the single colony in the deep-sea in-situ environment according to claim 4, and specifically comprises following steps:

S1: cleaning and sterilizing the device for separating the single colony in the deep-sea in-situ environment, and loading the device into the culture medium;

S2: injecting a gas into the separation operation incubator through the pressure control unit, so that a pressure value in the separation operation incubator is consistent with that of a microbial enrichment environment;

S3: activating the temperature control unit, so that the temperature of the separation operation incubator is consistent with that of the microbial enrichment environment;

S4: injecting a microbial bacterial liquid into the separation operation incubator through the liquid injection unit, controlling the sampling probe device to slide on the inner slide rail to dip the microbial bacteria liquid first, and then making the sampling probe device to be located on a surface of the culture medium to carry out streaking on the surface of the culture medium according to a certain trajectory;

S5: making separated microorganisms grow according to the trajectory, and observing the microorganisms in real time through the observation area;

S6: when a single colony is formed on the culture medium, activating the sampling unit, so that a temperature and a pressure of the sampling unit are consistent with those of the separation operation incubator; and S7: controlling the sampling probe device to select a single colony on the culture medium and transfer the single colony to the sampling unit containing a liquid culture medium to realize transfer and culture of a single colony under pressure-holding conditions.

13. A method for separating a single colony in a deep-sea in-situ environment, the method is realized by using the device for separating the single colony in the deep-sea in-situ environment according to claim 5, and specifically comprises following steps:

S1: cleaning and sterilizing the device for separating the single colony in the deep-sea in-situ environment, and loading the device into the culture medium;

S2: injecting a gas into the separation operation incubator through the pressure control unit, so that a pressure value in the separation operation incubator is consistent with that of a microbial enrichment environment;

S3: activating the temperature control unit, so that the temperature of the separation operation incubator is consistent with that of the microbial enrichment environment;

S4: injecting a microbial bacterial liquid into the separation operation incubator through the liquid injection unit, controlling the sampling probe device to slide on the inner slide rail to dip the microbial bacteria liquid first, and then making the sampling probe device to be located on a surface of the culture medium to carry out streaking on the surface of the culture medium according to a certain trajectory;

S5: making separated microorganisms grow according to the trajectory, and observing the microorganisms in real time through the observation area;

S6: when a single colony is formed on the culture medium, activating the sampling unit, so that a temperature and a pressure of the sampling unit are consistent with those of the separation operation incubator; and S7: controlling the sampling probe device to select a single colony on the culture medium and transfer the single colony to the sampling unit containing a liquid culture medium to realize transfer and culture of a single colony under pressure-holding conditions.

14. A method for separating a single colony in a deep-sea in-situ environment, the method is realized by using the device for separating the single colony in the deep-sea in-situ environment according to claim 6, and specifically comprises following steps:

S1: cleaning and sterilizing the device for separating the single colony in the deep-sea in-situ environment, and loading the device into the culture medium;

S2: injecting a gas into the separation operation incubator through the pressure control unit, so that a pressure value in the separation operation incubator is consistent with that of a microbial enrichment environment;

S3: activating the temperature control unit, so that the temperature of the separation operation incubator is consistent with that of the microbial enrichment environment;

S4: injecting a microbial bacterial liquid into the separation operation incubator through the liquid injection unit, controlling the sampling probe device to slide on the inner slide rail to dip the microbial bacteria liquid first, and then making the sampling probe device to be located on a surface of the culture medium to carry out streaking on the surface of the culture medium according to a certain trajectory;

S5: making separated microorganisms grow according to the trajectory, and observing the microorganisms in real time through the observation area;

S6: when a single colony is formed on the culture medium, activating the sampling unit, so that a temperature and a pressure of the sampling unit are consistent with those of the separation operation incubator; and S7: controlling the sampling probe device to select a single colony on the culture medium and transfer the single colony to the sampling unit containing a liquid culture medium to realize transfer and culture of a single colony under pressure-holding conditions.

15. A method for separating a single colony in a deep-sea in-situ environment, the method is realized by using the device for separating the single colony in the deep-sea in-situ environment according to claim 7, and specifically comprises following steps:

S1: cleaning and sterilizing the device for separating the single colony in the deep-sea in-situ environment, and loading the device into the culture medium;

S2: injecting a gas into the separation operation incubator through the pressure control unit, so that a pressure value in the separation operation incubator is consistent with that of a microbial enrichment environment;

S3: activating the temperature control unit, so that the temperature of the separation operation incubator is consistent with that of the microbial enrichment environment;

S4: injecting a microbial bacterial liquid into the separation operation incubator through the liquid injection unit, controlling the sampling probe device to slide on the inner slide rail to dip the microbial bacteria liquid first, and then making the sampling probe device to be located on a surface of the culture medium to carry out streaking on the surface of the culture medium according to a certain trajectory;

S5: making separated microorganisms grow according to the trajectory, and observing the microorganisms in real time through the observation area;

S6: when a single colony is formed on the culture medium, activating the sampling unit, so that a temperature and a pressure of the sampling unit are consistent with those of the separation operation incubator; and S7: controlling the sampling probe device to select a single colony on the culture medium and transfer the single colony to the sampling unit containing a liquid culture medium to realize transfer and culture of a single colony under pressure-holding conditions.

16. A method for separating a single colony in a deep-sea in-situ environment, the method is realized by using the device for separating the single colony in the deep-sea in-situ environment according to claim 8, and specifically comprises following steps:

S1: cleaning and sterilizing the device for separating the single colony in the deep-sea in-situ environment, and loading the device into the culture medium;

S2: injecting a gas into the separation operation incubator through the pressure control unit, so that a pressure value in the separation operation incubator is consistent with that of a microbial enrichment environment;

S3: activating the temperature control unit, so that the temperature of the separation operation incubator is consistent with that of the microbial enrichment environment;

S4: injecting a microbial bacterial liquid into the separation operation incubator through the liquid injection unit, controlling the sampling probe device to slide on the inner slide rail to dip the microbial bacteria liquid first, and then making the sampling probe device to be located on a surface of the culture medium to carry out streaking on the surface of the culture medium according to a certain trajectory;

S5: making separated microorganisms grow according to the trajectory, and observing the microorganisms in real time through the observation area;

S6: when a single colony is formed on the culture medium, activating the sampling unit, so that a temperature and a pressure of the sampling unit are consistent with those of the separation operation incubator; and S7: controlling the sampling probe device to select a single colony on the culture medium and transfer the single colony to the sampling unit containing a liquid culture medium to realize transfer and culture of a single colony under pressure-holding conditions.

* * * * *